United States Patent [19]

Burkart et al.

[11] Patent Number: 4,792,567
[45] Date of Patent: Dec. 20, 1988

[54] ACARICIDAL ARYL ARYLTHIEN-2-YL ETHENES

[75] Inventors: Susan E. Burkart, Trenton; Cesar Rodriguez, Cranbury; David M. Roush, Princeton, all of N.J.; Richard B. Phillips, Diamond Bar, Calif.

[73] Assignee: FMC Corporation, Philadelphia, Pa.

[21] Appl. No.: 60,188

[22] Filed: Jun. 9, 1987

[51] Int. Cl.$^4$ .................. A01N 43/02; C07F 7/02; C07D 409/00; C07D 333/08
[52] U.S. Cl. .................. 514/422; 514/438; 514/444; 548/406; 548/527; 549/4; 549/59; 549/77; 549/78; 549/79; 549/80
[58] Field of Search .................. 549/59, 80, 4, 77, 78, 549/79; 514/438, 444, 422; 548/406, 527

[56] References Cited

FOREIGN PATENT DOCUMENTS 5049273   9/1973   Japan .................. 549/59
0033660   3/1977   Japan .................. 549/80

OTHER PUBLICATIONS

Chem. Abs. 57:150476.

Beno et al., Collection Czechoslov. Chem. Commun., 1973, 38, 2734–2738.
Von Jurgen Liebscher, et al.—J. Pract. Chem., 1976, 318(5), 731–744.
Chem. Abstracts 80:36614u—Kovac et al., Chem. Zvesti, 1973, 27(4), 512–520.
Chem. Abstracts 70683a (1974), Juergen, et al, East German Pat. No. 98,681.
Chem. Abstracts 86:6381x, Juergen, et al., J. Pract. Chem., 1976, 318(5).

*Primary Examiner*—Alan Siegel
*Attorney, Agent, or Firm*—Robert L. Andersen; H. Robinson Ertelt

[57] ABSTRACT

Acaricidal aryl arylthien-2-yl ethenes of the formula

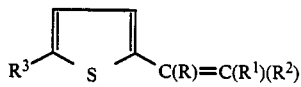

in which $R^2$ and $R^3$ are each an optionally substituted phenyl or thienyl group are disclosed and claimed.

6 Claims, No Drawings

ACARICIDAL ARYL ARYLTHIEN-2-YL ETHENES

The present invention relates to photoactivated acaricidal aryl-substituted arylthien-2-yl ethenes, agricultural compositions thereof, and to a method for controlling acarids therewith.

In accordance with the present invention, aryl-substituted arylthien-2-yl ethenes of formula I below are highly active photoactivated acaricides.

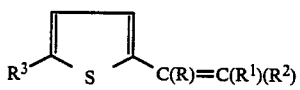

I in which R and $R^1$ are independently selected from hydrogen, halogen, lower alkyl, lower alkoxycarbonyl, and —$N(CO_2C_2H_5)(CH_2C_6H_{11})$ and $R^2$ and $R^3$ are each independently selected from the group consisting of phenyl which may be substituted with halogen, lower alkyl, lower alkoxy, haloalkyl, or dimethylpyrrolyl and thienyl which may be substituted with lower alkyl or trimethyl silyl.

Particularly desirable compounds of the invention are those compounds of formula I in which one of R and $R^1$ is selected from hydrogen and lower alkyl and the other of R and $R^1$ is selected from hydrogen, halogen, lower alkyl, lower alkoxycarbonyl and —N(-$CO_2C_2H_5)(CH_2C_6H_{11})$; $R^2$ is an aryl group selected from the group consisting of phenyl which may be substituted with lower alkyl, halogen, lower haloalkyl, or dimethylpyrrolyl and thienyl which may be substituted with lower alkyl or trimethyl silyl; $R^3$ is selected from phenyl or thienyl which may be substituted with lower alkyl.

In this specification and the claims, the terms described in this paragraph have the meanings set forth below. The terms "halo" and "halogen" mean chlorine, fluorine or bromine; the term "lower" modifying alkyl, alkoxy and the like means a straight or branched hydrocarbon chain of 1 to 6, preferably 1 to 4, carbon atoms. The term "halo" modifying alkyl or alkoxy or a like hydrocarbon means one or more hydrogen atoms of the hydrocarbon have been replaced with halogen.

The compounds of this invention are prepared by general techniques taken or adapted from chemical literature and/or methods well known to those skilled in the art. For example, reference is made to Tamao, et al., *Tetrahedron*, 38, 3347 (1982); Vilsmeier et al., *Ber.*, 60, 119 (1927); and Stevens et al., *J. Org. Chem.*, 37, 977 (1972). The examples which follow illustrate the methods for preparing the compounds of the invention.

EXAMPLE 1

SYNTHESIS OF 2-(4-METHYLPHENYL)-1-(5-PHENYLTHIENE-2-YL)ETHENE

Under a nitrogen atmosphere, a mixture of 0.7 gram (catalyst) of bis(1,3-diphenylphosphine)propane-nickel-(II) chloride in 200 mL of dry diethyl ether was stirred, and 40 grams (0.245 mole) of 2-bromothiophene was added. The mixture was cooled to 0° C., and 113 mL (0.328 mole) of phenylmagnesium bromide (3M in diethyl ether) was added during a 20 minute period. Upon complete addition the reaction mixture was allowed to warm to room temperature and then was heated at reflux for 16 hours. The reaction mixture was poured into 500 mL of an aqueous 10% hydrochloric acid solution and shaken. The organic layer was separated from the mixture and washed with distilled water. The organic layer was dried over anhydrous magnesium sulfate and filtered. The filtrate was concentrated under reduced pressure to a residue. This residue was distilled under vacuum to yield 36 grams of 2-phenylthiophene, b.p. 140° C. 3 mm, which slowly solidified upon standing.

Under a nitrogen atmosphere 75 mL of dimethylformamide was cooled to 0° C., and 15 mL of phosphorus oxychloride was added with stirring. The solution was allowed to warm to room temperature, and then a solution of 20.4 grams (0.127 mole) of 2-phenylthiophene in 20 mL of dimethylformamide was added in one portion. The reaction mixture was heated to 80° C. where it stirred for 24 hours. It was then poured into 250 mL of an aqueous, 10% sodium hydroxide solution containing 50 grams of ice. The resulting slurry was extracted with chloroform, and the extract was washed in succession with an aqueous solution saturated with sodium chloride and water. The organic phase was dried over anhydrous magnesium sulfate and filtered. TThe filtrate was concentrated under reduced pressure to a brown residue. Purification of this residue by column chromatography on silica gel, eluting with ethyl acetate:n-hexane (15:85) yielded 18.0 grams of 2-formyl-5-phenylthiophene.

To a stirred solution of 1.52 gram (0.008 mole) of 2-formyl-5-phenylthiophene and 2.0 grams (0.00820 mole) of diethyl 4-methylbenzylphosphonate in 40 mL of N,N-dimethylformamide was added 0.53 gram (0.0098 mole) of sodium methoxide. The reaction mixture was stirred at room temperature for approximately 18 hours and then was quenched with 50 mL of an aqueous solution saturated with ammonium chloride. A precipitate formed and was collected by filtration. The filter cake was washed with water. The washed solid was purified by column chromatography on silica gel, eluting with chloroform:n-hexane (10:90) yielded 1.1 gram of 2-(4-methylphenyl)-1-(5-phenylthien-2-yl)ethene as a solid, m.p. 159°-160° C.

EXAMPLE 2

SYNTHESIS OF 2-PHENYL-1-(5-PHENYLTHIEN-2-YL)-1-PROPENE

Under a nitrogen atmosphere 13.7 mL of a 2.6M solution of n-butyllithium in n-hexane was added to a cold (−78° C.) stirred solution of 5.2 grams (0.0325 mole) of 2-phenylthiophene in 61 mL of tetrahydrofuran. This mixture was stirred at −78° C. for 1.5 hours. To this cold mixture was added 2-phenylpropionaldehyde (4.6 gram, 0.0336 mole), and the mixture was stirred for 15 minutes. The mixture was allowed to warm to room temperature and stir for two days. The mixture was cooled to 0° C., and approximately 45 mL of 1.2 N hydrochloric acid was added. The organic phase was separated from the aqueous phase and the aqueous phase, was extracted with chloroform. The chloroform extract was combined with the organic phase and washed with an aqueous, ammonium chloride solution. The washed organic phase was dried over anhydrous magnesium sulfate and filtered. The filtrate was evaporated under reduced pressure leaving a residue. This residue was purified by column chromatography on silica gel, eluting with ethyl acetate:n-hexane (10:90), to yield 9.2 g of 2-phenyl-1-(5-phenylthien-2-yl)-1-propanol as an oil.

A stirred mixture of 8.0 grams (0.027 mole) of 2-phenyl-1-(5-phenylthien-2-yl)-1-propanol in 100 mL of concentrated hydrochloric acid was heated at reflux for 1.5 hours. The mixture was cooled and extracted with chloroform. The extract was washed with an aqueous solution saturated with sodium chloride and dried over anhydrous magnesium sulfate. The mixture was filtered, and the filtrate was evaporated under reduced pressure yielding a solid residue. Half of this residue was purified by column chromatography on silica gel, eluting with toluene:n-hexane (5:95). The remainder of the residue was purified by recrystallization from toluene and ethanol to yield a total of 4.0 grams of 2-phenyl-1-(5-phenylthien-2-yl)-1-propene as a solid, m.p. 115°–25° C.

EXAMPLE 3

SYNTHESIS OF 2-(4-CHLOROPHENYL)-1-(5'-METHYL-[2,2'-BITHIENYL]-5-YL)ETHENE

Under a nitrogen atmosphere 25 mL of 2.6M solution of n-butyllithium in hexane was added to a stirred, cold (−78° C.) solution of 9.8 grams (0.058 mole) of 2,2'-bithiophene in 150 mL of tetrahydrofuran. After addition, the mixture was stirred at −78° C. for 15 minutes and then was allowed to warm to 0° C. and stirred at this temperature for one hour. Dimethyl sulfate (5.8 mL, 0.061 mole) was added, and the mixture was allowed to warm to room temperature and stir for approximately 16 hours. This mixture was cooled to −78° C., and 25 mL of 2.6M solution of n-butyllithium was added. The reaction mixture was stirred at −78° C. for fifteen minutes and was then allowed to warm to 0° C. and stirred for one hour. While maintaining a temperature of 0° C., 5.3 mL (0.068 mole) of N,N-dimethylformamide was added. After addition, the mixture was allowed to warm to room temperature and stir for two hours. The mixture was quenched with 180 mL of 10% hydrochloric acid. After stirring for 20 minutes, the organic phase was removed and diluted with diethyl ether. The aqueous phase was retained. This organic phase was washed with 10% hydrochloric acid and an aqueous solution saturated with sodium chloride. The aqueous phase from above was extracted with chloroform. This extract was washed with an aqueous solution saturated with sodium chloride and then combined with the washed organic phase. This organic mixture was dried over anhydrous magnesium sulfate and filtered. The filtrate was evaporated under reduced pressure leaving an oil. This oil was purified by column chromatography on silica gel to yield 16.0 grams of 5-formyl-5'-methyl [2,2'-bithienyl] as an oil.

Under a nitrogen atmosphere, 0.12 gram (0.0050 mole) of sodium hydride was added to a stirred solution of 1.2 gram (0.0057 mole) of 5-formyl-5'-methyl[2,2'-bithienyl] and 1.7 gram (0.0064 mole) of diethyl 4-chlorobenzylphosphonate in 20 mL of N,N-dimethylformamide. The reaction mixture was stirred at room temperature for about three huurs. Analysis of the reaction mixture by thin layer chromatography indicated starting materials remained. Additional sodium hydride was added, and the mixture was stirred at room temperature for several hours. The reaction mixture was quenched with an aqueous solution saturated with ammonium chloride. This mixture was extracted several times with diethyl ether. The extracts were combined and washed with an aqueous solution saturated with sodium chloride. The washed extract was dried over anhydrous magnesium sulfate and filtered. The filtrate was evaporated under reduced pressure leaving a residue. This residue was purified by column chromatography on silica gel to yield 2-(4-chlorophenyl)-1-(5'-methyl[2,2'-bithienyl]-5-yl)ethene as a solid, m.p. 157°–162° C.

EXAMPLE 4

SYNTHESIS OF ETHYL N-CYCLOHEXYLMETHYL-N-[1-PHENYL-2-(5-PHENYL-2-THIENYL)ETHENE-1-YL]CARBAMATE

A stirred mixture of 10.0 grams (0.094 mole) of benzaldehyde and 11.0 grams (0.097 mole) of (cyclohexylmethyl)amine in 40 mL of chloroform was heated at reflux for five hours. Most of the solvent was removed by distillation leaving a chloroform solution containing N-(cyclohexylmethyl)phenylmethanimine.

The solution of N-(cyclohexylmethyl)phenylmethanimine in chloroform was diluted to 100 mL with fresh chloroform. This solution was stirred and cooled to −5° C. Ethyl chloroformate (11.0 mL, 0.12 mole) was added, and the mixture was stirred for ten minutes. Trimethyl phosphite (13.0 mL, 0.11 mole) was added, and the cold mixture was stirred for an additional ten minutes. The mixture was allowed to warm to room temperature and stir for 30 minutes. This mixture was poured slowly into an aqueous solution of potassium carbonate. The resultant mixture was extracted with chloroform. The extract was washed with an aqueous solution saturated with sodium chloride and then was dried over anhydrous magnesium sulfate. The dried solution was filtered, and the filtrate was evaporated under reduced pressure, leaving an oil. This oil was purified by column chromatography on silica gel to yield ethyl N-cyclohexylmethyl-N-[phenyl(dimethoxyphosphinyl)methyl]carbamate as an oil.

Under a nitrogen atmosphere n-butyllithium (1.3 mL of a 2.5M solution in hexane) was added to a stirred, cold (−78° C.) solution of 1.15 gram (0.00293 mole) of N-cyclohexylmethyl-N-[phenyl(dimethoxyphosphinyl)methyl]carbamate in approximately 20 mL of tetrahydrofuran. This mixture was stirred for about 30 minutes at −78° C. after which 2-formyl-5-phenylthiophene (0.51 gram, 0.0027 mole) was added. The mixture was allowed to gradually warm to room temperature and stir for four hours. The reaction mixture was quenched with dilute hydrochloric acid and was then extracted with chloroform. The extract was dried over anhydrous magnesium sulfate and filtered through celite. The filtrate was evaporated under reduced pressure to yield 0.6 gram of ethyl N-cyclohexylmethyl-N-[1-phenyl-2-(5-phenyl-2-thienyl)ethene-1-yl]carbamate as a red gel.

The nmr and ultraviolet spectra were consistent with the proposed structure. The ultraviolet spectrum was as follows: λmax nm (Log E): 350 (4.3); 347 (4.3); 344 (4.3); 261 (4.0); 224 (4.1).

The compounds of the invention which were made in accordance with the methods illustrated above are set forth in Table 1.

TABLE 1

| Compd No. | Name | M.P. (°C.) |
|---|---|---|
| 1 | 1-(5-Phenylthien-2-yl)-2-phenylethene | 158–160 |
| 2 | 2-(4-Fluorophenyl)-1-(5-phenylthien- | 149–150 |

TABLE 1-continued

| Compd No. | Name | M.P. (°C.) |
|---|---|---|
| | 2-yl)ethene | |
| 3 | 2-(4-Chlorophenyl)-1-(5-phenylthien-2-yl)ethene | 167–169 |
| 4 | E-2-(4-Bromophenyl)-1-(5-phenylthien-2-yl)ethene | 178–179 |
| 5 | 2-(4-Methylphenyl)-1-(5-phenylthien-2-yl)ethene | Example 1 |
| 6 | 2-[4-(1-Methylethyl)phenyl)]-1-(5-phenylthien-2-yl)ethene | 114–116 |
| 7 | 2-(4-Trifluoromethylphenyl)-1-(5-phenylthien-2-yl)ethene | 143–145 |
| 8 | 2-(4-Pentoxyphenyl)-1-(5-phenyl-thien-2-yl)ethene | 127–129 |
| 9 | 1-(5-phenylthien-2-yl)-2-[4-(2,5-dimethylpyrrol-1-yl)-phenyl)ethylene | 137–139 |
| 10 | 2-Chloro-2-phenyl-1-(5-phenylthien-2-yl)ethene | 65–80 |
| 11 | 2-Phenyl-1-(5-phenylthien-2-yl)-1-propene | Example 2 |
| 12 | Ethyl 2-phenyl-3-(5-phenylthien-2-yl)-2-propeneoate | Oil[1] |
| 13 | Ethyl E-2-phenyl-3-(5-phenylthien-2-yl)-2-propeneoate | 88–90 |
| 14 | Ethyl N—cyclohexylmethyl-N—[1-phenyl-2-(5-phenyl-2-thienyl)ethene-1-yl]-carbamate | Example 4 |
| 15 | 2-Chloro-2-(4-chlorophenyl)-1-(5-phenylthien-2-yl)ethene | 98–121 |
| 16 | 3-Phenyl-2-(5-phenylthien-2-yl)-2-butene | 56–65 |
| 17 | E-2-Phenyl-1-([2,2'-bithienyl]-5-yl)-ethene | 111–112 |
| 18 | E-2-(4-Chlorophenyl)-1-([2,2'-bithienyl]-5-yl)ethene | 143–145 |
| 19 | 2-Chloro-2-phenyl-1-([2,2'-bithienyl]-5-yl)ethene | 102–110 |
| 20 | 2-Phenyl-1-([2,2'-bithienyl]-5-yl)-1-propene | 95–115 |
| 21 | Ethyl N—methylcyclohexyl-N—[1-phenyl-2-([2,2'-bithienyl]-5-yl)ethene-1-yl]-carbamate | Oil[2] |
| 22 | 1-(5'-Methyl[2,2'-bithienyl]-5-yl)-2-phenylethene | 118–124 |
| 23 | 2-(4-Chlorophenyl)-1-(5'-methyl-[2,2'-bithienyl]-5-5-yl)ethene | Example 3 |
| 24 | 2-(2,6-Difluorophenyl)-1-(5'-methyl-[2,2'-bithienyl]-5-yl)ethene | 71–76 |
| 25 | 2-[4-(1-Methylethyl)phenyl]-1-(5'-methyl[2,2'-bithienyl]-5-yl)ethene | 105–106 |
| 26 | 2-(4-Trifluoromethylphenyl)-1-(5'-methyl[2,2'-bithienyl]-5-yl)ethene | 141–143 |
| 27 | 2-[4-(2-Fluoroethoxy)phenyl]-1-(5'-methyl[2,2'-bithienyl]-5-yl)ethene | 147–149 |
| 28 | 2-(4-Pentoxyphenyl)-1-(5'-methyl-[2,2'-bithienyl]-5-yl)ethene | 108–110 |
| 29 | 1-(5'-Methyl[2,2'-bithienyl]-5-yl)-2-[4-(2,5-dimethyl-1-pyrrolyl)phenyl]-ethene | 80–93 |
| 30 | 2-Chloro-1-(5'-methyl[2,2'-bithi-enyl]-5-yl)-2-phenyl-ethene | 86–90 |
| 31 | E-1-(5-Phenylthien-2-yl)-2-(thien-2-yl)ethene | 153–155 |
| 32 | 2-(5-Trimethylsilylthien-2-yl)-1-(5-phenylthien-2-yl)ethene | 123–125 |
| 33 | Ethyl N—cyclohexylmethyl-N—[1-(5-phenylthien-2-yl)-2-(2-thienyl)-ethene-1-yl]carbamate | Gel[3] |
| 34 | E-2-(Thien-2-yl)-1-([2,2'-bithienyl]-5-yl)ethene | 105–107 |
| 35 | E-2-(5-Methylthien-2-yl)-1-(5'-methyl-[2,2'-bithienyl]-5-yl)ethene | 104–107 |

[1] NMR; (CDCl$_3$,δ): 1.27 (3H,t,J=7 Hz); 4.25 (2H,q,J=7 Hz); 7.10 (1H,s); 7.1–7.6 (1H,m); 8.0 (1H,s)
[2] NMR; (CDCl$_3$,δ): 0.90 (t,J=7 Hz), 1.02 (t,J=7 Hz), 1.20 (t,J=7 Hz), 1.3 (m), 1.5–1.8 (m), 3.15 (d,J=7 Hz), 4.08 (q,J=7 Hz), 4.14 (q,J=7 Hz), 6.63 (s), 6.72 (d), 6.95–7.5 (m)
[3] Ultraviolet spectrum - λmax nm (Log E): 362 (4.0); 294 (4.2); 287 (4.1); 229 (4.1)

The compounds of this invention are useful for control of pests which feed upon the above ground portions of agricultural crops, and are particularly effective against acarids such as mites. They are also effective in some instances in controlling insects.

In the normal use of the thienyl ethene compounds of the present invention, the compounds usually will not be employed free from admixture or dilution, but ordinarily will be used in a suitable formulated composition compatible with the method of application and comprising an acaricidally effective amount of the compound. The compounds of this invention, like most pesticidal agents, may be blended with the agriculturally acceptable surface-active agents and carriers normally employed for facilitating the dispersion of active ingredients, recognizing the accepted fact that the formulation and mode of application of an acaricide may affect the activity of the material. The present compounds may be applied, for example, as sprays, dusts, or granules to the area where pest control is desired, the type of application varying of course with the pest and the environment. Thus, the compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the present compounds. The granule particles are relatively large, a diameter of about 400–2500 microns typically. The particles are either impregnated with the compound of the invention from solution or coated with the compound, adhesive sometimes being employed. Granules generally contain 0.05–10%, preferably 0.5–5%, active ingredient as the acaricidally effective amount.

Dusts are admixtures of the acaricidal compounds, with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the acaricide. These finely divided solids have an average particle size of less than about 50 microns. A typical dust formulation useful for controlling acarids contains 1 part of thienyl ethene compound and 99 parts of talc.

The thienyl ethene compounds of the present invention may be made into liquid concentrates by dissolution or emulsification in suitable liquids and into solid concentrates by admixture with talc, clays, and other known solid carriers used in the pesticide art. The concentrates are compositions containing, as an acaricidally effective amount, about 5–50% thienyl ethene compound and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

A typical 50% wettable powder formulation would consist of 50.0% (wt/wt) of active ingredient 22.0% attapulgite diluent, 22.0% kaolin diluent, and 6.0% sodium salts of sulfonated Kraft lignin emulsifier.

Typical carriers for solid concentrates (also called wettable powders) include fuller's earth, clays, silicas, and other highly absorbent, readily wetted inorganic diluents. A solid concentrate formulation useful for controlling acarids contains 1.5 parts each of sodium lignosulfonate and sodium lauryl-sulfate as wetting agents, 25 parts of Compound 5 and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

A typical 50 gram per liter emulsifiable concentrate formulation would consist of 5.90% (wt/wt) of a compound of the invention; as emulsifiers: 1.80% of a blend of the calcium salt of dodecylbenzene sulfonate and a nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the acaricidal composition.

Other useful formulations include simple solutions of the active ingredient in a solvent in which it is completely soluble at the desired concentration, such as acetone or other organic solvents.

An insecticidally or acaricidally effective amount of thienyl compound in an insecticidal or acaricidal composition diluted for application is normally in the range of about 0.001% to about 8% by weight. Many variations of spraying and dusting compositions known in the art may be used by substituting the thienyl compounds of this invention into compositions known or apparent in the art.

The insecticidal or acaricidal compositions of this invention may be formulated with other active ingredients, including other acaricides, nematicides, insecticides, fungicides, plant growth regulators, fertilizers, etc. In using the compositions to control acarids, it is only necessary that an acaricidally effective amount of thienyl ethene compound be applied to the locus where control is desired. Such locus may, e.g., be the acarids themselves, plants upon which the acarids feed, or the acarid habitat. When the locus is soil, e.g., soil in which agricultural crops are or will be planted, the active compound may be applied to and optionally incorporated into the soil. For most applications, an insecticidally or acaricidally effective amount will be about 50 to 750 g per hectare, preferably 150 g to 500 g per hectare.

The acaricidal activity of the thienyl ethene compounds whose preparation is described above was evaluated as follows:

The thienyl compounds were tested for acaricidal activity under near ultraviolet light (wavelength 340–360 nanometers) at an intensity of 1600–2400 microwatts/cm$^2$ using test procedures adapted to the organisms in th test. Regardless of the organism, foliage of whole plants or foliage removed from whole plants was sprayed to runoff with a 10% acetone-0.25% octylphenoxypolyethoxyethanol-water solution containing up to 250 ppm of the test compound.

Leaves infested with adult twospotted spider mites (*Tetranychus urticae*) were removed from culture plants and cut into segments containing 50–75 female mites. Each segment was placed on the upper leaf surface of a whole pinto bean (*Phaseolus vulgaris*) plant. After the mites had migrated to the under surfaces of the leaves, the leaf segments used to infest were removed and each plant sprayed with test chemical as described above.

After the plants had dried, the entire plant and pot were placed in metal trays in a hood. A supply of water in the tray kept the plants turgid. Tests were conducted against both susceptible and phosphate resistant strains.

The test results were collected and recorded at the end of a 24 hour or 48 hour exposure period. The data obtained under ultraviolet irradiation appear in Table 2.

TABLE 2

| | ACARICIDAL ACTIVITY | | | |
|---|---|---|---|---|
| Cmpd No. | Rate (ppm) | Exposure Time (Hrs) | % Kill[4] TSM-R | TSM-S |
| 1 | 50 | 48 | 84 | 100 |
| 2 | 50 | 24 | — | 98 |
| 3 | 50 | 24 | — | 89 |
| 4 | 100 | 24 | — | 82 |
| 5 | 50 | 24 | 79 | 100 |
| 6 | 50 | 24 | — | 100 |
| 7 | 50 | 24 | — | 81 |
| 8 | 100 | 24 | — | 32 |
| 9 | 100 | 24 | — | 5 |
| 10 | 50 | 24 | 98 | 100 |
| 11 | 50 | 48 | 86 | 100 |
| 12 | 100 | 24 | — | 86 |
| 13 | 50 | 24 | — | 82 |
| 14 | 100 | 24 | — | 94 |
| 15 | 50 | 24 | — | 100 |
| 16 | 50 | 24 | 99 | 100 |
| 17 | 100 | 48 | 98 | 100 |
| 18 | 50 | 24 | — | 92 |
| 19 | 50 | 24 | 12 | 100 |
| 20 | 100 | 48 | 94 | 100 |
| 21 | 50 | 24 | — | 19 |
| 22 | 50 | 24 | 70 | 100 |
| 23 | 50 | 24 | 17 | 99 |
| 24 | 50 | 24 | — | 85 |
| 25 | 50 | 24 | — | 100 |
| 26 | 50 | 24 | 26 | 100 |
| 27 | 50 | 24 | — | 74 |
| 28 | 100 | 24 | — | 55 |
| 29 | 100 | 24 | — | 87 |
| 30 | 50 | 24 | 100 | 100 |
| 31 | 100 | 24 | — | 68 |
| 32 | 50 | 24 | — | 96 |
| 33 | 50 | 24 | — | 66 |
| 34 | 50 | 24 | 100 | 82 |

TABLE 2-continued

| Cmpd No. | ACARICIDAL ACTIVITY | | | |
|---|---|---|---|---|
| | Rate (ppm) | Exposure Time (Hrs) | % Kill[4] TSM-R | TSM-S |
| 35 | 50 | 24 | — | 91 |

[4]Acarid species:
TSM = twospotted spider mite (*Tetranychus urticae*)
-R = Strain is resistant to phosphate insecticides
-S = Strain is not resistant to any types of insecticides

What is claimed is:

1. An acaricidal compound of the formula

in which R and $R^1$ are independently selected from hydrogen, halogen, lower alkyl, lower aloxycarbonyl, and $N(CO_2C_2H_5)(CH_2C_6H_{11})$; and $R^2$ and $R^3$ are each independently selected from the group consisting of phenyl which may be substituted with halogen, lower alkyl, lower alkoxy, trifluoromethyl, or dimethylpyrrolyl and thienyl which may be substituted with lower alkyl or trimethyl silyl, with the proviso that at least one of $R^2$ and $R^3$ is other than phenyl or alkylphenyl.

2. The compound of claim 1 in which one of R and $R^1$ is selected from hydrogen and lower alkyl and the other of R and $R^1$ is selected from hydrogen, halogen, lower alkyl, lower alkoxycarbonyl and —N(-$CO_2C_2H_5)(CH_2C_6H_{11})$; $R^2$ is selected from the group consisting of phenyl which may be substituted with lower alkyl, halogen, trifluoromethyl or dimethylpyrrolyl and thienyl which may be substituted with lower alkyl or trimethyl silyl; $R^3$ is selected from phenyl or thienyl which may be substituted with lower alkyl.

3. An acaricidal composition comprising an acaricidal amount of a compound of the formula

in which R and $R^1$ are independently selected from hydrogen, halogen, lower alkyl, lower alkoxycarbonyl, and $N(CO_2C_2H_5)(CH_2C_6H_{11})$ and $R^2$ and $R^3$ are each independently selected from the group consisting of phenyl which may be substituted with halogen, lower alkyl, lower alkoxy, trifluoromethyl, or dimethylpyrrolyl and thienyl which may be substituted with lower alkyl or trimethyl silyl in admixture with an agriculturally acceptable carrier, diluent, or adjuvant, with the proviso that at least one of $R^2$ and $R^3$ is other than phenyl or alkylphenyl.

4. The acaricidal composition of claim 3 in which one of R and $R^1$ is selected from hydrogen and lower alkyl and the other of R and $R^1$ is selected from hydrogen, halogen, lower alkyl, lower alkoxycarbonyl and —N(-$CO_2C_2H_5)(CH_2C_6H_{11})$; $R^2$ is selected from the group consisting of phenyl which may be substituted with lower alkyl, halogen, trifluoromethyl, or dimethylpyrrolyl and thienyl which may be substituted with lower alkyl or trimethyl silyl; $R^3$ is selected from phenyl or thienyl which may be substituted with lower alkyl.

5. A method for controlling acarids which comprises applying to a locus where control is desired an acaricidally effective amount of the compound of the formula

in which R and $R^1$ are independently selected from hydrogen, halogen, lower alkyl, lower alkoxycarbonyl, and $N(CO_2C_2H_5)(CH_2C_6H_{11})$ and $R^2$ and $R^3$ are each independently selected from the group consisting of phenyl which may be substituted with halogen, lower alkyl, lower alkoxy, haloalkyl, or dimethylpyrrolyl and thienyl which may be substituted with lower alkyl or trimethyl silyl.

6. The method of claim 5 in which one of R and $R^1$ is selected from hydrogen and lower alkyl and the other of R and $R^1$ is selected from hydrogen, halogen, lower alkyl, lower alkoxycarbonyl and —N(-$CO_2C_2H_5)(CH_2C_6H_{11})$; $R^2$ is selected from the group consisting of phenyl which may be substituted with lower alkyl, halogen, lower haloalkyl, or dimethylpyrrolyl and thienyl which may be substituted with lower alkyl or trimethyl silyl; $R^3$ is selected from phenyl or thienyl which may be substituted with lower alkyl.

* * * * *

UNITED STATES PATENT AND TRADEMARK OFFICE
CERTIFICATE OF CORRECTION

PATENT NO. : 4,792,567

DATED : December 20, 1988

INVENTOR(S) : Susan E. Burkart, Cesar Rodriguez, David M. Roush, Richard B. Phillips It is certified that error appears in the above-identified patent and that said Letters Patent is hereby corrected as shown below:

Column 3, line 16, "115°-25°C" should read -- 115°-125°C --.

Signed and Sealed this

Twenty-seventh Day of November, 1990

Attest:

HARRY F. MANBECK, JR.

*Attesting Officer*　　　*Commissioner of Patents and Trademarks*